(12) United States Patent
Gibson

(10) Patent No.: US 9,320,248 B2
(45) Date of Patent: Apr. 26, 2016

(54) POCONO LETTUCE VARIETY

(71) Applicant: PROGENY ADVANCED GENETICS, Salinas, CA (US)

(72) Inventor: Darryn Gibson, Prunedale, CA (US)

(73) Assignee: Progeny Advanced Genetics, Salinas, CA (US)

( * ) Notice: Subject to any disclaimer, the term of this patent is extended or adjusted under 35 U.S.C. 154(b) by 173 days.

(21) Appl. No.: 14/042,271

(22) Filed: Sep. 30, 2013

(65) Prior Publication Data

US 2014/0101794 A1    Apr. 10, 2014

Related U.S. Application Data

(60) Provisional application No. 61/709,843, filed on Oct. 4, 2012.

(51) Int. Cl.
*A01H 5/12* (2006.01)

(52) U.S. Cl.
CPC ........................................ *A01H 5/12* (2013.01)

(58) Field of Classification Search
None
See application file for complete search history.

(56) References Cited

U.S. PATENT DOCUMENTS

2011/0083235 A1 *    4/2011    Gibson .................... 800/305

* cited by examiner

*Primary Examiner* — Eileen B O Hara
*Assistant Examiner* — Stephen Uyeno
(74) *Attorney, Agent, or Firm* — Morrison & Foerster LLP

(57) ABSTRACT

A new lettuce variety designated 'Pocono' is described. 'Pocono' is an iceberg lettuce variety exhibiting stability and uniformity.

11 Claims, No Drawings

POCONO LETTUCE VARIETY

CROSS REFERENCE TO RELATED APPLICATION

This application claims the benefit under 35 §USC 119(e) of prior U.S. Provisional Patent Application No. 61/709,843, filed Oct. 4, 2012, the disclosure of which is hereby incorporated by reference in its entirety.

FIELD

This invention relates to the field of plant breeding. In particular, this invention relates to new lettuce, *Lactuca sativa*, variety, 'Pocono'.

BACKGROUND

Lettuce is an increasingly popular crop. Worldwide lettuce consumption continues to increase. As a result of this demand, there is a continued need for new lettuce varieties. In particular, there is a need for improved romaine lettuce varieties that exhibit improved growth habits, bolting and tip burn tolerance, and disease resistance.

SUMMARY

In order to meet these needs, the present invention is directed to an improved iceberg lettuce variety that exhibits vigorous growth, increased weight, and increased yield. In particular, the present invention is directed to lettuce, *Lactuca sativa*, seed designated as 'Pocono' having ATCC Accession Number PTA-120617. The present invention is further directed to a lettuce head isolated from a *Lactuca sativa* plant produced by growing 'Pocono' lettuce seed having ATCC Accession Number PTA-120617. The present invention is further directed to a *Lactuca sativa* plant having all the physiological and morphological characteristics of a *Lactuca sativa* plant produced by growing 'Pocono' lettuce seed having ATCC Accession Number PTA-120617. The present invention is further directed to an $F_1$ hybrid *Lactuca sativa* plant having 'Pocono' as a parent, where 'Pocono' lettuce seed is grown from 'Pocono' seed having ATCC Accession Number PTA-120617.

The present invention is further directed to lettuce, *Lactuca sativa* plants and lettuce heads isolated therefrom produced by growing 'Pocono' lettuce seed. The present invention is further directed to a *Lactuca sativa* plant and the lettuce head isolated therefrom having all the physiological and morphological characteristics of a *Lactuca sativa* plant produced by growing 'Pocono' lettuce seed having ATCC Accession Number PTA-120617. The present invention is further directed to an $F_1$ hybrid lettuce, *Lactuca sativa* plant and a head isolated therefrom grown from the seed having 'Pocono' as a parent wherein 'Pocono' is grown from 'Pocono' lettuce seed having ATCC Accession Number PTA-120617.

The present invention is further directed to pollen isolated from 'Pocono' lettuce plants. The present invention is further directed to ovules isolated from 'Pocono' lettuce plants. The present invention is further directed to tissue culture of 'Pocono' lettuce plants.

The present invention is further directed to a method of selecting lettuce plants by: a) growing more than one 'Pocono' lettuce plant, where the plants are grown from lettuce seed having ATCC Accession Number PTA-120617; and b) selecting a plant from step a). The present invention is further directed to lettuce plants and seeds produced therefrom, where the lettuce plants and seeds are isolated by the selection method of the invention.

The present invention is further directed to a method of breeding lettuce by crossing a lettuce plant with a plant grown from 'Pocono' lettuce seed having ATCC Accession Number PTA-120617. The present invention is further directed to lettuce plants, heads isolated therefrom, and seeds produced therefrom, where the lettuce plant is isolated by the breeding method of the invention.

DETAILED DESCRIPTION

Definitions

In order to more clearly understand the invention, the following definitions are provided:

Iceberg Lettuce: Iceberg lettuce, *Lactuca sativa* L. var. *capitala* L. is also known as 'crisp head' lettuce. Iceberg lettuce is a lettuce plant type that forms a firm, spherical head formed with tightly folded brittle textured foliage. Internal color ranges from white to yellow to light green. The wrapper leaves surrounding the head are wider than they are long. Leaf margins can vary by type, being entire, undulating, or frilled. Wrapper leaf color ranges from yellow green to dark green.

Core Length: Core length is the length of the internal lettuce stem. Core length is measured from the base of the cut head to the tip of the core.

Core Diameter: Core diameter is the diameter of the lettuce stem at the base of the cut head.

Head Diameter: Head diameter is the diameter of the vertically sliced lettuce plant head at its widest horizontal point, perpendicular to the stem.

Head Length: Head length is the diameter of the vertically sliced lettuce plant head as measured from the base of the cut stem to the cap leaf.

Average Head Diameter: Average head diameter is an average of the measured head diameter and head length of the lettuce head.

Average Head Diameter: Core Length Ratio: The ratio of the average head diameter to core length is indicative of the percentage of useable product produced by the lettuce plant.

Frame Diameter: The frame diameter is a measurement of the lettuce plant diameter at its widest point. The measurement of frame diameter is from the outer most wrapper leaf tip to outer most wrapper leaf tip.

Head Weight: Head weight is the weight of the marketable lettuce plant, cut and trimmed to market specifications.

Rogueing: Rogueing is the process in lettuce seed production where undesired plants are removed from a variety. The plants are removed because they differ physically from the general desired expressed characteristics of the variety. The differences can be related to size, color, maturity, leaf texture, leaf margins, growth habit, or any other characteristic that distinguishes the plant.

Market Stage: Market stage is the stage when a lettuce plant is ready for commercial lettuce harvest. In the case of a romaine lettuce variety, a romaine plant is at a marketable state when the heart has some density and the head has reached an adequate size and weight.

Taking into account these definitions, the present invention is directed to seeds of the lettuce variety 'Pocono', plants produced by growing 'Pocono' lettuce seeds, head isolated or harvested from the plants, one or more plants selected from a collection of 'Pocono' plants and seeds derived or produced therefrom; plants produced by crossing a lettuce plant with a 'Pocono' lettuce plant and seeds derived or produced therefrom.

'Pocono' is an iceberg lettuce variety that is distinct to all known iceberg lettuce varieties due to its dark green color, large heading, and improved texture for late fall and early winter plantings in regions such as Yuma, Ariz.

Through extensive field trialing and screenings, 'Pocono' has demonstrated to have a dark green color, large heading, improved texture, and to be well adapted for late fall and early winter plantings in regions such as Yuma, Ariz.

'Pocono' was evaluated in multiple trials and evaluated for improved head and frame size, dark green color, and smoother texture.

'Pocono' has been extensively trialed in Yuma, Ariz., and was selected for large head and frame size, dark green color and an improved smoother texture. 'Pocono' was also selected for growth during winter plantings in Yuma, Ariz.

As evaluated in multiple seed production fields and commercial plantings for 2 generations, 'Pocono' has been observed to be uniform and stable without variants.

As described herein, lettuce variety 'Pocono' has numerous distinguishing characteristics.

| A. Variety Description Information | |
|---|---|
| Plant Type: | Iceberg |
| Seed: | |
| Seed Color: | White |
| Light Dormancy: | Light not required |
| Heat Dormancy: | Susceptible |
| Cotyledons: | |
| Shape of Cotyledons: | Intermediate |
| Shape of Fourth Leaf: | Broad/Elongated |
| Length/Width Index of Fourth Leaf: | 26 |
| Apical Margin: | Finely Dentate |
| Basal Margin: | Finely Dentate |
| Undulation: | Flat |
| Green Color: | Dark Green |
| Anthocyanin: | |
| Distribution: | Absent |
| Rolling: | Absent |
| Cupping: | Absent |
| Reflexing: | Lateral Margins |
| Mature Leaves: | |
| Margin: | |
| Incision Depth (Deepest penetration of the margin): | Moderate |
| Indentation (Finest Division of the Margin): | Crenate |
| Undulation of the Apical Margin: | Moderate |
| Green Color: | Dark |
| Anthocyanin Distribution: | Absent |
| Size: | Large |
| Glossiness: | Moderate |
| Blistering: | Slight/moderate |
| Leaf Thickness: | Intermediate |
| Trichomes: | Absent |

| B. Comparison to Most Similar Variety | | |
|---|---|---|
| Characteristic | 'Pocono' | 'Speedway' |
| Head Shape | Spherical | Spherical |
| Head Size Class | Large | Large |
| Head Count per Carton | 24 | 24 |
| Head Weight | 924 | 889 |
| Head Firmness | Firm | Firm |
| Shape | Round | Round/Pointed |
| Midrib | Moderately Raised | Moderately Raised |
| Bolting Class | Medium | Medium |
| Bolter Leaves | Curved | Curved |
| Margin | Dentate | Dentate |
| Color | Medium Green | Medium Green |
| Terminal Inflorescence | Present | Present |
| Lateral Shoots (above head) | Present | Present |
| Basal Side Shoots | Absent | Absent |

| C. Growing Season | | |
|---|---|---|
| Season | 'Pocono' | 'Speedway' |
| Spring area | Not Adapted | Desert South west |
| Summer area | Not Adapted | Not Adapted |
| Fall area | Huron CA, and Desert Southwest | Not Adapted |
| Winter area: | Desert Southwest | Not Adapted |

| D. Diseases and Stress Reactions | | |
|---|---|---|
| Disease or Stress | 'Pocono' | 'Speedway' |
| Virus | N/A | NA |
| Big Vein: | N/A | N/A |
| Lettuce Mosaic: | N/A | N/A |
| Cucumber Mosaic: | N/A | N/A |
| Broad Bean Wilt: | N/A | N/A |
| Turnip Mosaic: | N/A | N/A |
| Best Western Yellows: | N/A | N/A |
| Lettuce Infectious Yellows: | N/A | N/A |

| E. Fungi/Bacteria | | |
|---|---|---|
| Fungal/Bacterial | 'Pocono' | 'Speedway' |
| Corky Root Rot (*Pythium* Root Rot): | N/A | N/A |
| Downy Mildew (Races I, IIA, III): | N/A | N/A |
| Powdery Mildew: | N/A | N/A |
| *Sclerotinia* Rot: | N/A | N/A |
| Bacterial Soft Rot (*Pseudomonas* spp. & others): Not tested | | |
| *Botrytis* (Gray Mold): | N/A | N/A |
| Other: Corky Root Rot (*Rhizomonas suberifaciens*): | N/A | N/A |

| F. Insects | | |
|---|---|---|
| Insects | 'Pocono' | 'Speedway' |
| Cabbage Loopers: | N/A | N/A |
| Root Aphids: | N/A | N/A |
| Green Peach Aphid: | N/A | N/A |

| G. Physiological/Stress | | |
|---|---|---|
| Stress | 'Pocono' | 'Speedway' |
| Tipburn | N/A | N/A |
| Heat | N/A | N/A |

-continued

G. Physiological/Stress

| Stress  | 'Pocono' | 'Speedway' |
| ------- | -------- | ---------- |
| Drought | N/A      | N/A        |
| Cold    | Tolerant | Tolerant   |
| Salt    | N/A      | N/A        |

H. Post Harvest

| Characteristic                                            | 'Pocono' | 'Speedway' |
| --------------------------------------------------------- | -------- | ---------- |
| Pink Rib                                                  | N/A      | N/A        |
| Russet Spotting                                           | N/A      | N/A        |
| Rusty Brown Discoloration                                 | N/A      | N/A        |
| Internal Rib Necrosis (Blackheart, Gray Rib, Gray Streak) | N/A      | N/A        |
| Brown Stain                                               | N/A      | N/A        |

Breeding and Selection

The present invention is further directed to the use of 'Pocono' lettuce in breeding and selection of new varieties.

A. Breeding

In lettuce breeding, lines are selected for their appropriate characteristics. For example, one line may be selected for bolt tolerance in the fall growing conditions of the desert production locations of California and Arizona. Another line may be selected for the size, color, and texture of the lettuce head. Crosses are made, for example, to produce a dark green, sure heading iceberg lettuce with improved texture and size for fall plantings in Yuma, Ariz. and Huron, Calif.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self-pollinating possibilities, is very tedious and time consuming when a large number of crosses are to be made. The breeders have therefore adapted a well-documented and modified method of making crosses more efficiently using these methods. This particular cross was made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers in order to keep track.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908 both of which are hereby incorporated by reference in their entirety for the purpose of providing details on the techniques well known in the art.

B. Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

DEPOSIT INFORMATION

A deposit of the lettuce variety 'Pocono' is maintained by Progeny Advanced Genetics, having an address at 590A Works Street, Salinas, Calif. 93901, United States of America. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the American Type Culture Collection, (ATCC), P.O. Box 1549, MANASSAS, Va. 20108 USA.

At least 2500 seeds of lettuce variety 'Pocono' were deposited on Oct. 10, 2013 according to the Budapest Treaty in the American Type Culture Collection (ATCC), ATCC Patent Depository, 10801 University Boulevard, Manassas, Va., 20110, USA. The deposit has been assigned ATCC number PTA-120617. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed for the enforceable life of the patent.

The deposit will be maintained in the ATCC depository, which is a public depository, for a period of 30 years, or 5 years after the most recent request, or for the effective life of the patent, whichever is longer, and will be replaced if a deposit becomes nonviable during that period.

This invention will be better understood by reference to the following non-limiting Examples.

EXAMPLES

Example 1

General Trialing Method

The following steps illustrate the general trialing method of the invention:

I. Set Up
 1. A trial is set up to compare one or more lines. Parental lines and related varieties are identified.
 2. Primary slots are identified.
 3. Necessary accession lines are located and purchased/received from seed dealers or growers.
 4. All varieties are assigned a number to maintain integrity and anonymity.
 5. Trials are set up in with all necessary varieties. Variety arrangement for trial is diagramed.

II. Planting
 1. Commercial plantings are located by contacting commercial growers during the planting slot recommended for the variety.
 2. A field is located during commercial planting and the necessary rows and area is marked off.
 3. Varieties are planted according to a diagram, generally in 100 foot ranges.
 4. All varieties are planted in same manner to mimic the planting of the commercial variety as closely as possible.
 5. A trial map is drawn diagramming the trial, the trial location in the field and directions to the field.

III. Maintenance
 1. All varieties are treated identically. Plants are watered, fertilized, and treated to control pests in the same manner as other lettuce plants in the commercial field.
 2. The trial is thinned to separate the plants for optimum growth.

Example 2

Comparative Analysis

'Pocono' is a new and distinct variety of iceberg lettuce that most closely resembles the commercial variety 'Speedway'.

'Pocono' is a vanguard type iceberg lettuce variety adapted to the early winter and spring harvest of the desert South West and Huron lettuce production regions of California and Arizona. 'Pocono' is large heading and large framed, widely adapted variety, with improved heading characteristics, and improved resistance to tip burn and bolting.

Compared to 'Speedway', 'Pocono' is larger heading, and adapted to slightly cooler harvest periods. 'Pocono' can be planted in the desert South West lettuce production region between October $1^{st}$ and October $10^{th}$, for harvest in January. In addition to this slot, 'Pocono' can again be planted in the desert south west between October $25^{th}$ and November $15^{th}$, for harvest in February. 'Speedway', needing more heat units to produce a marketable head, is planted between November $15^{th}$ and December $10^{th}$ for harvest in March. 'Speedway' is generally not planted in the fall slot because of its smaller size. With the increased vigor of Toconos', compared to 'Speedway', 'Pocono' is larger heading, and framed, but will also have higher cores and is more susceptible to tip burn if grown at the same time period as 'Speedway'.

'Pocono' has a significantly longer core length than 'Speedway'. 'Pocono' is significantly larger heading than 'Speedway'.

Core elongation characteristics of the 'Pocono' iceberg lettuce variety were measured from six independent trials. Three of these independent trials were conducted in the winter of Year 10 in Yuma, Ariz. (TABLE 1A). The other three independent trials were conducted in the winter of Year 11 in Yuma, Ariz. (TABLE 1B). All trials from Year 10 and Year 11 included the lettuce variety 'Speedway' so that the core elongation characteristics of 'Pocono' could be directly compared to its most similar variety.

TABLE 1A

Year 10 Trials: Core Length Evaluation of 'Pocono' and 'Speedway'

| Plant | Trial 1 Core Length (mm) | | Trial 2 Core Length (mm) | | Trial 3 Core Length (mm) | |
|---|---|---|---|---|---|---|
| | Pocono | Speedway | Pocono | Speedway | Pocono | Speedway |
| 1 | 45.0 | 36.0 | 42.0 | 38.0 | 40.0 | 30.0 |
| 2 | 45.0 | 36.0 | 41.0 | 35.0 | 42.0 | 35.0 |
| 3 | 48.0 | 32.0 | 41.0 | 35.0 | 4.0 | 35.0 |
| 4 | 42.0 | 36.0 | 45.0 | 32.0 | 45.0 | 32.0 |
| 5 | 43.0 | 36.0 | 45.0 | 35.0 | 48.0 | 35.0 |
| 6 | 45.0 | 38.0 | 48.0 | 32.0 | 45.0 | 36.0 |
| 7 | 45.0 | 35.0 | 45.0 | 32.0 | 42.0 | 33.0 |
| 8 | 46.0 | 35.0 | 42.0 | 32.0 | 42.0 | 31.0 |
| 9 | 48.0 | 32.0 | 42.0 | 30.0 | 45.0 | 32.0 |
| 10 | 41.0 | 35.0 | 42.0 | 35.0 | 43.0 | 34.0 |
| 11 | 41.0 | 32.0 | 45.0 | 36.0 | 46.0 | 38.0 |
| 12 | 40.0 | 32.0 | 40.0 | 30.0 | 47.0 | 32.0 |
| 13 | 45.0 | 35.0 | 40.0 | 32.0 | 41.0 | 30.0 |
| 14 | 43.0 | 35.0 | 45.0 | 38.0 | 46.0 | 30.0 |
| 15 | 42.0 | 32.0 | 42.0 | 35.0 | 45.0 | 35.0 |
| 16 | 40.0 | 30.0 | 41.0 | 32.0 | 45.0 | 35.0 |
| 17 | 40.0 | 32.0 | 43.0 | 36.0 | 48.0 | 32.0 |
| 18 | 40.0 | 32.0 | 45.0 | 35.0 | 42.0 | 31.0 |
| 19 | 48.0 | 35.0 | 46.0 | 30.0 | 42.0 | 35.0 |
| 20 | 48.0 | 36.0 | 42.0 | 32.0 | 42.0 | 36.0 |
| 21 | 45.0 | 36.0 | 42.0 | 36.0 | 41.0 | 30.0 |
| 22 | 46.0 | 32.0 | 42.0 | 38.0 | 40.0 | 30.0 |
| 23 | 46.0 | 31.0 | 45.0 | 31.0 | 40.0 | 30.0 |
| 24 | 46.0 | 31.0 | 42.0 | 34.0 | 48.0 | 32.0 |
| 25 | 45.0 | 35.0 | 40.0 | 32.0 | 47.0 | 35.0 |
| 26 | 47.0 | 38.0 | 40.0 | 35.0 | 46.0 | 36.0 |
| 27 | 43.0 | 36.0 | 48.0 | 32.0 | 45.0 | 39.0 |
| 28 | 42.0 | 35.0 | 45.0 | 35.0 | 42.0 | 38.0 |
| 29 | 42.0 | 32.0 | 40.0 | 36.0 | 43.0 | 35.0 |
| 30 | 48.0 | 35.0 | 35.0 | 35.0 | 41.0 | 36.0 |

TABLE 1A-continued

Year 10 Trials: Core Length Evaluation of 'Pocono' and 'Speedway'

| | Trial 1 Core Length (mm) | | Trial 2 Core Length (mm) | | Trial 3 Core Length (mm) | |
|---|---|---|---|---|---|---|
| Plant | Pocono | Speedway | Pocono | Speedway | Pocono | Speedway |
| Average | 44.2 | 34.1 | 42.7 | 33.9 | 42.4 | 33.6 |
| Stan dev | 2.70E+00 | 2.19E+00 | 2.74E+00 | 2.39E+00 | 7.69E+00 | 2.70E+00 |
| T test | 4.97E−09 | | 2.90E−19 | | 1.74E−07 | |
| Probability % | 100.0 | | 100.0000 | | 100.0000 | |
| % Difference | 29.5 | | 26.1 | | 26.3 | |
| Confidence Int | 0.0310 | 0.0250 | 0.0314 | 0.0273 | 0.0881 | 0.0309 |
| Range of Var min* | 44.14 | 34.07 | 42.67 | 33.84 | 42.35 | 33.57 |
| Range of Var max* | 44.20 | 34.13 | 42.73 | 33.89 | 42.52 | 33.63 |

*Range of variation among means of statistically significant differences at the 95% level using the confidence interval, [C] = mean +/− {SD × SE}

TABLE 1B

Year 11 Trials: Core Length Evaluation of 'Pocono' and 'Speedway'

| | Trial 1 Core Length (mm) | | Trial 2 Core Length (mm) | | Trial 3 Core Length (mm) | |
|---|---|---|---|---|---|---|
| Plant | Pocono | Speedway | Pocono | Speedway | Pocono | Speedway |
| 1 | 45.0 | 35.0 | 44.0 | 35.0 | 41.0 | 35.0 |
| 2 | 46.0 | 32.0 | 48.0 | 32.0 | 41.0 | 35.0 |
| 3 | 41.0 | 30.0 | 46.0 | 36.0 | 42.0 | 32.0 |
| 4 | 48.0 | 30.0 | 48.0 | 31.0 | 48.0 | 36.0 |
| 5 | 48.0 | 35.0 | 47.0 | 30.0 | 47.0 | 34.0 |
| 6 | 7.0 | 35.0 | 42.0 | 30.0 | 45.0 | 35.0 |
| 7 | 45.0 | 32.0 | 42.0 | 30.0 | 45.0 | 38.0 |
| 8 | 42.0 | 32.0 | 43.0 | 32.0 | 46.0 | 32.0 |
| 9 | 41.0 | 30.0 | 48.0 | 35.0 | 48.0 | 32.0 |
| 10 | 40.0 | 30.0 | 49.0 | 35.0 | 42.0 | 32.0 |
| 11 | 40.0 | 30.0 | 41.0 | 35.0 | 42.0 | 32.0 |
| 12 | 40.0 | 30.0 | 45.0 | 34.0 | 48.0 | 35.0 |
| 13 | 46.0 | 30.0 | 42.0 | 36.0 | 42.0 | 36.0 |
| 14 | 48.0 | 30.0 | 47.0 | 33.0 | 40.0 | 30.0 |
| 15 | 42.0 | 35.0 | 48.0 | 32.0 | 45.0 | 30.0 |
| 16 | 2.0 | 32.0 | 46.0 | 33.0 | 45.0 | 31.0 |
| 17 | 42.0 | 32.0 | 42.0 | 33.0 | 40.0 | 35.0 |
| 18 | 42.0 | 30.0 | 48.0 | 32.0 | 45.0 | 34.0 |
| 19 | 41.0 | 35.0 | 45.0 | 38.0 | 45.0 | 38.0 |
| 20 | 40.0 | 35.0 | 46.0 | 36.0 | 42.0 | 36.0 |
| 21 | 48.0 | 36.0 | 49.0 | 32.0 | 48.0 | 35.0 |
| 22 | 47.0 | 35.0 | 42.0 | 35.0 | 47.0 | 39.0 |
| 23 | 45.0 | 38.0 | 48.0 | 32.0 | 42.0 | 35.0 |
| 24 | 42.0 | 32.0 | 45.0 | 32.0 | 41.0 | 35.0 |
| 25 | 42.0 | 35.0 | 47.0 | 35.0 | 40.0 | 38.0 |
| 26 | 45.0 | 32.0 | 41.0 | 36.0 | 46.0 | 36.0 |
| 27 | 46.0 | 32.0 | 45.0 | 36.0 | 48.0 | 32.0 |
| 28 | 48.0 | 36.0 | 46.0 | 32.0 | 42.0 | 32.0 |
| 29 | 45.0 | 35.0 | 41.0 | 30.0 | 42.0 | 35.0 |
| 30 | 44.0 | 32.0 | 42.0 | 35.0 | 48.0 | 32.0 |
| Average | 41.3 | 32.8 | 45.1 | 33.4 | 44.1 | 34.2 |
| Stan dev | 1.04E+01 | 2.40E+00 | 2.68E+00 | 2.21E+00 | 2.84E+00 | 2.42E+00 |
| T test | 5.28E−05 | | 7.07E−26 | | 6.48E−21 | |
| Probability % | 99.9947 | | 100.0000 | | 100.0000 | |
| % Difference | 25.9 | | 34.9 | | 28.8 | |
| Confidence Int | 0.1189 | 0.0275 | 0.0307 | 0.0253 | 0.0326 | 0.0277 |
| Range of Var min* | 41.15 | 32.74 | 45.07 | 33.41 | 44.07 | 34.21 |
| Range of Var max* | 41.39 | 32.79 | 45.13 | 33.46 | 44.13 | 34.26 |

*Range of variation among means of statistically significant differences at the 95% level using the confidence interval, [C] = mean +/− {SD × SE}

As can be seen from TABLE 1A and 1B, the average core length of 'Pocono' ranged between 41.1 mm and 45.1 mm over the six trials. In contrast, 'Speedway' was observed to have an average core length ranging between 32.8 mm and 34.2 mm over the six trials. Overall, in the six trials conducted over two years, 'Pocono' consistently had a statistically significant longer core than 'Speedway' at the 95% confidence level.

In addition to core length evaluation, head diameter characteristics of the 'Pocono' iceberg lettuce variety were measured from six independent trials. Three of these independent trials were conducted in the winter of Year 10 in Yuma, Ariz.

(TABLE 2A). The other three independent trials were conducted in the winter of Year 11 in Yuma, Ariz. (TABLE 2B). All trials from Year 10 and Year 11 included the lettuce variety 'Speedway' so that the head diameter characteristics of 'Pocono' could be directly compared to its most similar variety.

TABLE 2A

Year 10 Trials: Head Diameter Evaluation of 'Pocono' and 'Speedway'

| Plant | Trial 1 Head diam (mm) | | Trial 2 Head diam (mm) | | Trial 3 Head diam (mm) | |
|---|---|---|---|---|---|---|
| | Pocono | Speedway | Pocono | Speedway | Pocono | Speedway |
| 1 | 148.0 | 138.0 | 148.0 | 138.0 | 149.0 | 135.0 |
| 2 | 152.0 | 136.0 | 145.0 | 132.0 | 148.0 | 135.0 |
| 3 | 154.0 | 135.0 | 145.0 | 130.0 | 148.0 | 136.0 |
| 4 | 152.0 | 135.0 | 151.0 | 130.0 | 148.0 | 138.0 |
| 5 | 153.0 | 135.0 | 148.0 | 135.0 | 150.0 | 130.0 |
| 6 | 157.0 | 134.0 | 148.0 | 135.0 | 152.0 | 130.0 |
| 7 | 152.0 | 136.0 | 145.0 | 136.0 | 148.0 | 136.0 |
| 8 | 148.0 | 133.0 | 145.0 | 136.0 | 151.0 | 132.0 |
| 9 | 159.0 | 136.0 | 145.0 | 132.0 | 152.0 | 130.0 |
| 10 | 156.0 | 139.0 | 142.0 | 136.0 | 152.0 | 136.0 |
| 11 | 154.0 | 140.0 | 145.0 | 130.0 | 154.0 | 136.0 |
| 12 | 154.0 | 145.0 | 146.0 | 132.0 | 150.0 | 132.0 |
| 13 | 152.0 | 152.0 | 148.0 | 132.0 | 148.0 | 132.0 |
| 14 | 150.0 | 136.0 | 150.0 | 134.0 | 150.0 | 135.0 |
| 15 | 150.0 | 130.0 | 152.0 | 135.0 | 158.0 | 134.0 |
| 16 | 158.0 | 132.0 | 149.0 | 132.0 | 152.0 | 138.0 |
| 17 | 152.0 | 135.0 | 147.0 | 132.0 | 156.0 | 132.0 |
| 18 | 149.0 | 154.0 | 153.0 | 135.0 | 150.0 | 130.0 |
| 19 | 152.0 | 138.0 | 140.0 | 135.0 | 153.0 | 135.0 |
| 20 | 149.0 | 139.0 | 145.0 | 135.0 | 152.0 | 136.0 |
| 21 | 151.0 | 140.0 | 148.0 | 130.0 | 150.0 | 132.0 |
| 22 | 150.0 | 132.0 | 148.0 | 130.0 | 152.0 | 130.0 |
| 23 | 152.0 | 135.0 | 145.0 | 136.0 | 154.0 | 136.0 |
| 24 | 145.0 | 136.0 | 156.0 | 132.0 | 156.0 | 135.0 |
| 25 | 149.0 | 136.0 | 145.0 | 135.0 | 154.0 | 134.0 |
| 26 | 152.0 | 138.0 | 158.0 | 130.0 | 154.0 | 136.0 |
| 27 | 150.0 | 135.0 | 154.0 | 130.0 | 152.0 | 130.0 |
| 28 | 150.0 | 132.0 | 148.0 | 130.0 | 151.0 | 135.0 |
| 29 | 156.0 | 136.0 | 147.0 | 132.0 | 153.0 | 132.0 |
| 30 | 153.0 | 136.0 | 152.0 | 130.0 | 148.0 | 135.0 |
| Average | 152.0 | 137.1 | 147.9 | 132.9 | 151.5 | 133.8 |
| Stan dev | 3.13E+00 | 5.21E+00 | 3.97E+00 | 2.48E+00 | 2.66E+00 | 2.53E+00 |
| T test | 2.38E−19 | | 6.65E−25 | | 4.62E−34 | |
| Probability % | 100.00 | | 100.00 | | 100.00 | |
| % Difference | −10.8 | | −11.3 | | −13.3 | |
| Confidence Int | 0.0359 | 0.0597 | 0.0455 | 0.0284 | 0.0305 | 0.0289 |
| Range of Var min* | 151.93 | 137.07 | 147.89 | 132.87 | 151.47 | 133.74 |
| Range of Var max* | 152.00 | 137.19 | 147.98 | 132.93 | 151.53 | 133.80 |

*Range of variation among means of statistically significant differences at the 95% level using the confidence interval, [C] = mean +/− {SD × SE}

TABLE 2B

Year 11 Trials: Head Diameter Evaluation of 'Pocono' and 'Speedway'

| Plant | Trial 1 Head diam (mm) | | Trial 2 Head diam (mm) | | Trial 3 Head diam (mm) | |
|---|---|---|---|---|---|---|
| | Pocono | Speedway | Pocono | Speedway | Pocono | Speedway |
| 1 | 148.0 | 135.0 | 145.0 | 135.0 | 149.0 | 135.0 |
| 2 | 147.0 | 135.0 | 149.0 | 135.0 | 148.0 | 136.0 |
| 3 | 148.0 | 136.0 | 148.0 | 136.0 | 152.0 | 136.0 |
| 4 | 148.0 | 136.0 | 145.0 | 140.0 | 152.0 | 136.0 |
| 5 | 152.0 | 136.0 | 145.0 | 136.0 | 152.0 | 136.0 |
| 6 | 153.0 | 136.0 | 152.0 | 138.0 | 154.0 | 136.0 |
| 7 | 149.0 | 132.0 | 148.0 | 130.0 | 152.0 | 134.0 |
| 8 | 154.0 | 130.0 | 151.0 | 132.0 | 152.0 | 138.0 |
| 9 | 156.0 | 136.0 | 150.0 | 135.0 | 152.0 | 138.0 |
| 10 | 152.0 | 136.0 | 149.0 | 135.0 | 151.0 | 135.0 |
| 11 | 150.0 | 134.0 | 148.0 | 134.0 | 150.0 | 130.0 |
| 12 | 149.0 | 136.0 | 146.0 | 136.0 | 150.0 | 132.0 |
| 13 | 145.0 | 130.0 | 152.0 | 130.0 | 150.0 | 132.0 |
| 14 | 148.0 | 130.0 | 151.0 | 132.0 | 152.0 | 132.0 |
| 15 | 151.0 | 130.0 | 157.0 | 132.0 | 154.0 | 135.0 |
| 16 | 147.0 | 132.0 | 156.0 | 130.0 | 147.0 | 136.0 |
| 17 | 146.0 | 132.0 | 153.0 | 135.0 | 148.0 | 132.0 |

TABLE 2B-continued

Year 11 Trials: Head Diameter Evaluation of 'Pocono' and 'Speedway'

| Plant | Trial 1 Head diam (mm) | | Trial 2 Head diam (mm) | | Trial 3 Head diam (mm) | |
|---|---|---|---|---|---|---|
| | Pocono | Speedway | Pocono | Speedway | Pocono | Speedway |
| 18 | 152.0 | 132.0 | 152.0 | 134.0 | 154.0 | 134.0 |
| 19 | 149.0 | 135.0 | 149.0 | 136.0 | 152.0 | 134.0 |
| 20 | 153.0 | 130.0 | 148.0 | 135.0 | 150.0 | 132.0 |
| 21 | 148.0 | 130.0 | 151.0 | 135.0 | 148.0 | 133.0 |
| 22 | 147.0 | 136.0 | 150.0 | 132.0 | 146.0 | 134.0 |
| 23 | 146.0 | 135.0 | 153.0 | 130.0 | 146.0 | 135.0 |
| 24 | 148.0 | 132.0 | 147.0 | 135.0 | 152.0 | 130.0 |
| 25 | 145.0 | 138.0 | 146.0 | 132.0 | 154.0 | 132.0 |
| 26 | 152.0 | 136.0 | 145.0 | 138.0 | 152.0 | 130.0 |
| 27 | 152.0 | 138.0 | 148.0 | 136.0 | 148.0 | 135.0 |
| 28 | 150.0 | 134.0 | 142.0 | 135.0 | 150.0 | 135.0 |
| 29 | 150.0 | 136.0 | 157.0 | 130.0 | 150.0 | 136.0 |
| 30 | 140.0 | 138.0 | 154.0 | 132.0 | 148.0 | 134.0 |
| Average | 149.2 | 134.1 | 149.6 | 134.0 | 150.5 | 134.1 |
| Stan dev | 3.25E+00 | 2.68E+00 | 3.74E+00 | 2.63E+00 | 2.35E+00 | 2.19E+00 |
| T test | 2.60E−27 | | 3.97E−26 | | 2.13E−35 | |
| Probability % | 100.00 | | 100.00 | | 100.00 | |
| % Difference | −11.3 | | −11.6 | | −12.2 | |
| Confidence Int | 0.0372 | 0.0307 | 0.0428 | 0.0301 | 0.0268 | 0.0250 |
| Range of Var min* | 149.13 | 134.04 | 149.52 | 134.00 | 150.47 | 134.07 |
| Range of Var max* | 149.20 | 134.10 | 149.61 | 134.06 | 150.53 | 134.13 |

*Range of variation among means of statistically significant differences at the 95% level using the confidence interval, [C] = mean +/− {SD × SE}

As can be seen from TABLE 2A and 2B, the average head diameter of 'Pocono' ranged between 147.9 mm and 152.0 mm over the six trials. In contrast, 'Speedway' was observed to have an average head diameter ranging between 132.9 mm and 137.1 mm over the six trials. Overall, in the six trials conducted over two years, 'Pocono' consistently had a statistically significant larger head diameter than 'Speedway' at the 95% confidence level.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed:

1. *Lactuca sativa* seed designated as 'Pocono' having, representative sample of seed having been deposited under ATCC Accession Number PTA-120617.

2. A *Lactuca sativa* plant produced by growing the seed of claim 1.

3. A lettuce head isolated from the plant of claim 2.

4. A *Lactuca sativa* plant having all the physiological and morphological characteristics of the *Lactuca sativa* plant of claim 2.

5. An $F_1$ hybrid *Lactuca sativa* plant having 'Pocono' as a parent where 'Pocono' is grown from the seed of claim 1.

6. Pollen of the plant of claim 2.

7. An ovule of the plant of claim 2.

8. Tissue culture of the plant of claim 2.

9. A method of selecting lettuce, comprising:
   a) growing more than one plant from the seed of claim 1; and
   b) selecting a plant from step a).

10. A *Lactuca sativa* plant selected by the method of claim 9.

11. *Lactuca sativa* seed produced from the *Lactuca sativa* plant of claim 10.

* * * * *